(12) United States Patent
Lion

(10) Patent No.: US 6,438,451 B1
(45) Date of Patent: Aug. 20, 2002

(54) INTEGRATED SYSTEM AND METHOD OF VENDING PRESCRIPTION MEDICATIONS USING A NETWORK OF REMOTELY DISTRIBUTED, AUTOMATED DISPENSING UNITS

(76) Inventor: Nicholas Lion, P.O. Box 365, Kingston, NJ (US) 08528

( * ) Notice: Subject to any disclaimer, the term of this patent is extended or adjusted under 35 U.S.C. 154(b) by 0 days.

(21) Appl. No.: 10/017,524

(22) Filed: Dec. 7, 2001

Related U.S. Application Data

(62) Division of application No. 09/358,063, filed on Jul. 21, 1999, now Pat. No. 6,330,491.

(51) Int. Cl.[7] .............................................. G06F 7/00
(52) U.S. Cl. ...................................... 700/237; 700/241
(58) Field of Search .............................. 700/231, 232, 700/237, 241, 244; 221/2

(56) References Cited

U.S. PATENT DOCUMENTS

| | | | | |
|---|---|---|---|---|
| 3,917,045 A | * | 11/1975 | Williams et al. | 194/7 |
| 5,377,864 A | * | 1/1995 | Blechl et al. | 221/2 |
| 5,460,294 A | * | 10/1995 | Williams | 221/2 |
| 5,819,981 A | * | 10/1998 | Cox | 221/2 |
| 5,950,630 A | * | 9/1999 | Portwood et al. | 128/897 |
| 5,993,046 A | * | 11/1999 | McGrady et al. | 364/479.01 |
| 6,032,155 A | * | 2/2000 | De La Huerga | 700/104 |
| 6,330,491 B1 | * | 12/2001 | Lion | 700/237 |

* cited by examiner

Primary Examiner—Christopher P. Ellis
Assistant Examiner—Khoi H. Tran
(74) Attorney, Agent, or Firm—Brian K. Dinicola

(57) ABSTRACT

A network of interactive, self-service, medication dispensing kiosks that are each adaptable to contain an inventory of, for example, 200 to 1600 different drugs, as may be currently obtained directly from a local storefront, mail order, or "cyber" pharmacy. With the exception of periodic maintenance or inventory replenishment, the kiosks constructed in accordance with a preferred embodiment of the invention are unmanned. By strategically locating the dispensing kiosks of the present invention in easily accessible public locations on a regional or national basis, and stocking the same with an inventory of frequently prescribed medications for which a patient is likely to have an exigent need, an on-line (Internet) or mail order pharmacy may offer a level of convenient access to emergency medications and pharmaceutical services that is at least as complete and comprehensive as that offered by the conventional storefront pharmacy.

6 Claims, 4 Drawing Sheets

ID AND METHOD OF
INTEGRATED SYSTEM AND METHOD OF VENDING PRESCRIPTION MEDICATIONS USING A NETWORK OF REMOTELY DISTRIBUTED, AUTOMATED DISPENSING UNITS

REFERENCE TO RELATED APPLICATIONS

This patent application is a divisional of U.S. patent application Ser. No. 09/358,063, filed on Jul. 21, 1999, now U.S. Pat. No. 6,330,491.

BACKGROUND OF THE INVENTION

1. Field of the Invention

The present invention relates to the dispensing of prescription medications and, in particular, to a network of merchandising kiosks for the automated dispensing of such medications.

2. Discussion of the Background Art

With the advent of mail order and online ("cyber") pharmacies accessible via the Internet, most all medically prescribed prescription (Rx), as well as non-prescription drugs, and general health & beauty aids, can be shipped to the consumer within 2–5 days by regular mail or overnight by an express courier service. While such modes of delivery may be satisfactory in many situations—particularly those in which a patient on maintenance medication is refilling a prescription for which he or she has a recurring therapeutic need—there are other situations in which the applicable time delay is unacceptable. Illustratively, the patient may have an immediate need, with urgent or emergency implications, to take a medication such, for example, as an antibiotic drug prescribed by his or her physician to treat a bacterial infection.

Immediate initiation of some therapies is often imperative and highly beneficial to the treatment of disease—as in the case of bacterial infections as well as in other cases such, for example, as those for which analgesic, antipyretic, antiemetic and combination formulations for nausea and vomiting are prescribed. Regardless of whether the physician is in a position to provide the patient with an initial dosage of the prescribed medication, in the aforementioned situation the patient will find it necessary to seek a local community pharmacy to fill the antibiotic prescription ordered by the physician.

A need therefore exists for an integrated Rx-drug delivery/dispensing system which neither suffers from an inability to address a patient's requirement for an immediately available supply of medication nor requires a patient to abandon a preferred online Internet or mail order pharmacy in favor of a less economical, local community or "storefront" pharmacy.

SUMMARY OF THE INVENTION

The aforementioned deficiencies are addressed and an advance is made in the art by a network of interactive, self-service, Rx drug vending machines or kiosks that are each adaptable to contain an inventory of, for example, 200 to 1600 different drugs, as may be currently obtained directly from a local storefront, mail order, or "cyber" pharmacy. With the exception of periodic maintenance or inventory replenishment, the kiosks constructed in accordance with a preferred embodiment of the invention are unmanned. By strategically locating the dispensing kiosks of the present invention in easily accessible public locations on a regional or national basis, and stocking the same with an inventory of frequently prescribed medications, including Rx drugs, for which a patient is likely to have an exigent need, an online Internet or mail order pharmacy may offer a level of access to emergency medications and pharmaceutical services that is at least as complete and comprehensive as that offered by the conventional storefront pharmacy.

BRIEF DESCRIPTION OF THE DRAWINGS

The foregoing and other objects, features and advantages of the invention will be apparent from the following more particular description of exemplary embodiments of the invention, as illustrated in the accompanying drawings in which like reference characters refer to the same parts throughout the different views.

DETAILED DESCRIPTION OF THE INVENTION

Figure 1:
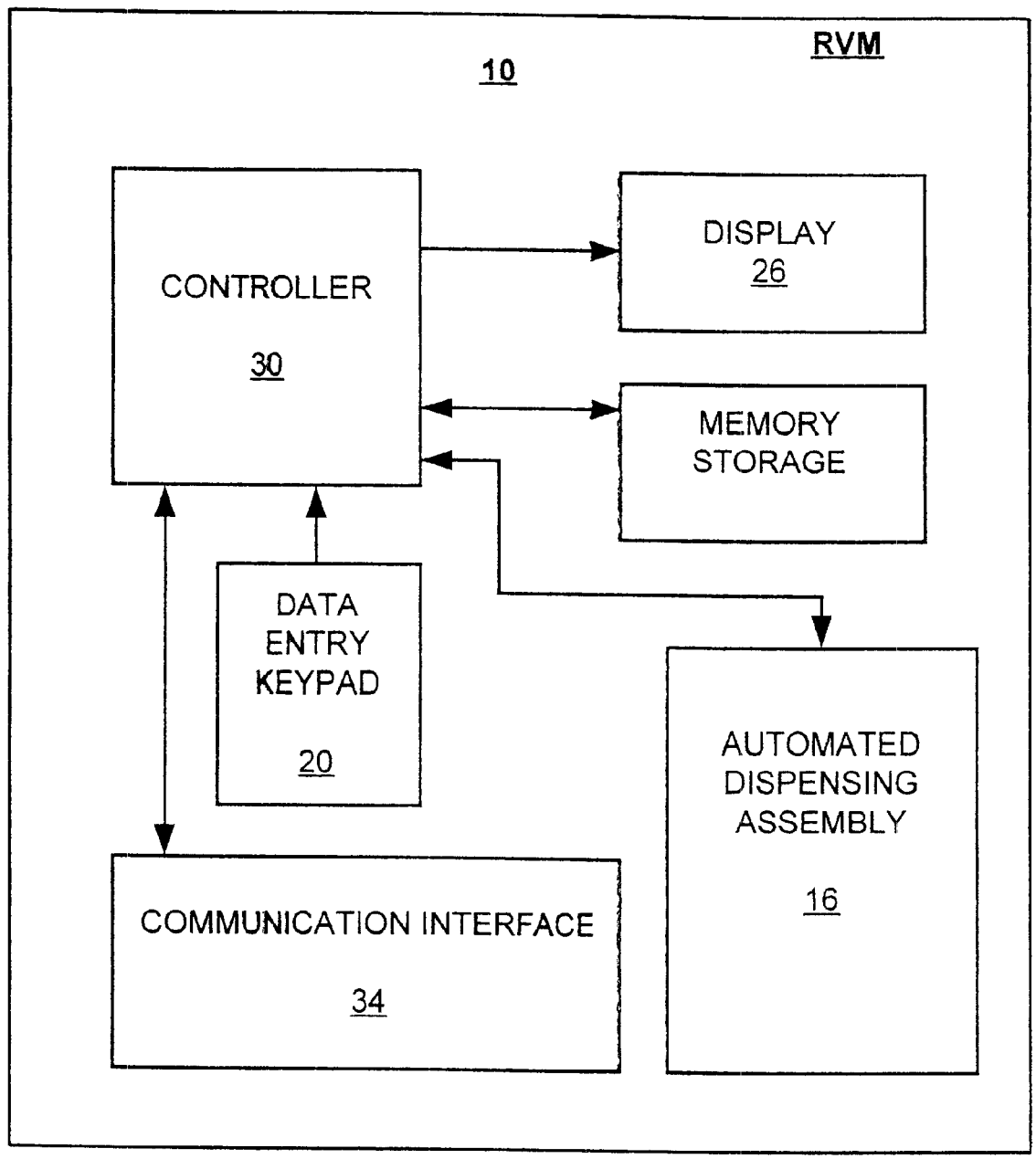
FIG. 1 is a schematic block diagram representing a representative dispensing Rx vending machine (RVM) unit constructed in accordance with an illustrative embodiment of the present invention.

With initial reference to FIG. 1, there is shown a perspective view of a remote, automated, dispensing Rx vending machine (RVM) unit 10 configured to distribute prescription medications directly to a patient/consumer in accordance with the teachings of the present invention. As will be described in more detail later, in a preferred embodiment of the invention, a network of such RVM units are provided—with each containing an inventory of 200 to 1600 different prescription medications, as may be currently obtained directly from a local storefront or mail order pharmacy.

Initially, it should be noted that the specific mechanisms and structure employed by each RVM unit as unit 10 to perform the storage and controlled dispensing of prescription medications is not deemed to be a critical aspect of the present invention. However, in accordance with an especially preferred form of the invention, an automated prescription medication dispensing system of the type described in detail in U.S. Pat. Nos. 5,812,410 and 5,838,575, is employed in order to facilitate the bulk storage of the respective medications so as to thereby allow the number of dosage units supplied to a given consumer to be dispensed in the quantity stipulated by the prescribing physician. U.S. Pat. Nos. 5,812,410 and 5,838,575 are expressly incorporated herein in their entirety and reference may be had to either of them for details on the storage and dispensing of dosage units. Of course, any apparatus capable of initiating dispensing of drugs and other therapeutic compounds without the intervention of a local operator other than the consumer, in response to a properly authenticated request by a consumer, may be utilized without departing from the spirit and scope of the present invention. It will therefore be readily appreciated by those skilled in the art that an RVM unit constructed in accordance with the present invention may be configured to dispense not only solid dosage units, but also ointments, creams, liquids, prepackaged dosage units, injectable solutions, and the like. In light of the limited shelf life of some therapeutic compounds, it may be desirable to equip the RVM unit with means (not shown) for separately storing the active and inert ingredients so that mixing may be deferred until the time of distribution to the consumer.

Figure 2:
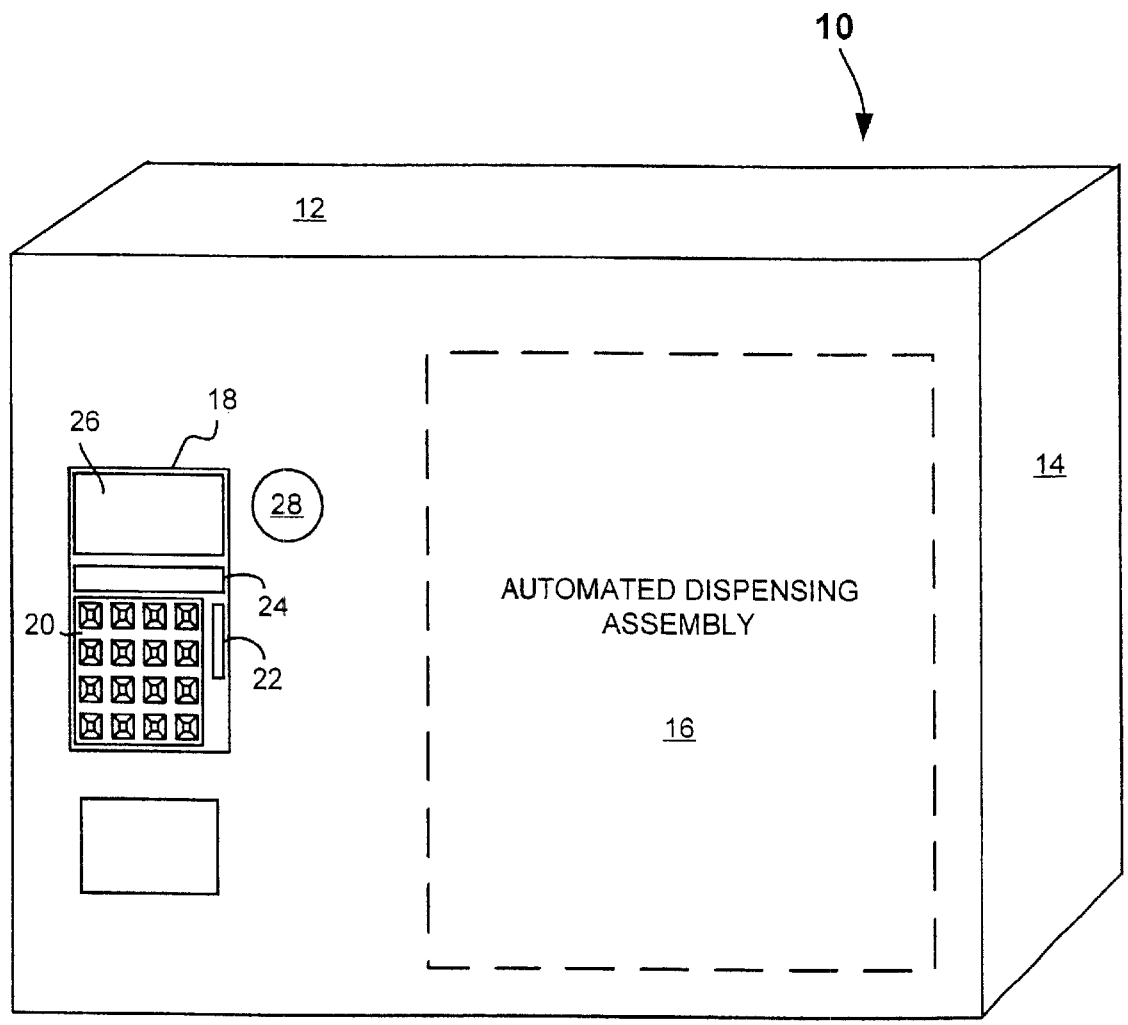
FIG. 2 is a perspective view depicting an RVM unit employed by the present invention.

In any event, and with reference now to FIG. 2, it will be seen that each RVM unit 10 may be readily fitted, in the manner of a kiosk, to available wall space or central floor space at many commercial establishments or other convenient public locations without undue cost or sacrificing security. With the exception of necessary power and communication connections (such as a telephone line), an RVM unit constructed in accordance with the present invention requires no special electrical or plumbing connections, and may occupy a footprint of as little as 40 inches by 80 inches, depending upon the number of unique drugs inventoried therein. As more or less inventory is required, the physical footprint dimensions of the RVM unit can be adjusted. Each RVM unit 10 is normally positioned in proximity to areas of high pedestrian traffic at a commercial establishment where Rx-needing patients have convenient access. In a typical setting, the RVM unit 10 might be set in an available corridor adjacent a hospital, Doctor's office, or grocery store. A relatively high visibility location which is convenient to periodic monitoring to provide a degree of security is especially preferred.

The RVM enclosure 12 can be constructed to any number of shapes. It can also be constructed using a variety of conventional metal and wood framing techniques to provide an aesthetically pleasing appearance and any desired degree of relative security. A variety of accent arrangements can be provided, depending upon the aesthetics of the mounting location and/or user preference. The enclosure 12 includes a hinged panel 14 and a stationary panel 16.

Mounted to one side of the enclosure 12 is an authentication data input panel 18 that comprises, for example, a numeric keypad 20 to accommodate the entry of a pre-assigned identification (ID) or transaction code assigned to the particular subscribing patient/consumer by an issuing online (Internet) or mail order pharmacy, and/or an electronic card reader or the like 22 enabling the consumer to both establish his or her identity and render payment by debit transaction to an ATM or personal credit card, if the transaction for the Rx drug product has not already been prepaid. In the illustrative example depicted in FIG. 2, panel 18 further includes a face plate 24 containing graphical information and a cathode ray tube (CRT), computer monitor, or other display screen 26. A computer controller 30 (FIG. 1) is mounted behind the face plate 24. The face plate 24 is printed over with appropriate operating instructions. An audio speaker 28 (FIG. 1), is also mounted to the enclosure 12 in close proximity to the panel 18 to broadcast audio instructions to assist the customer and messages to attract customers.

Figure 3:
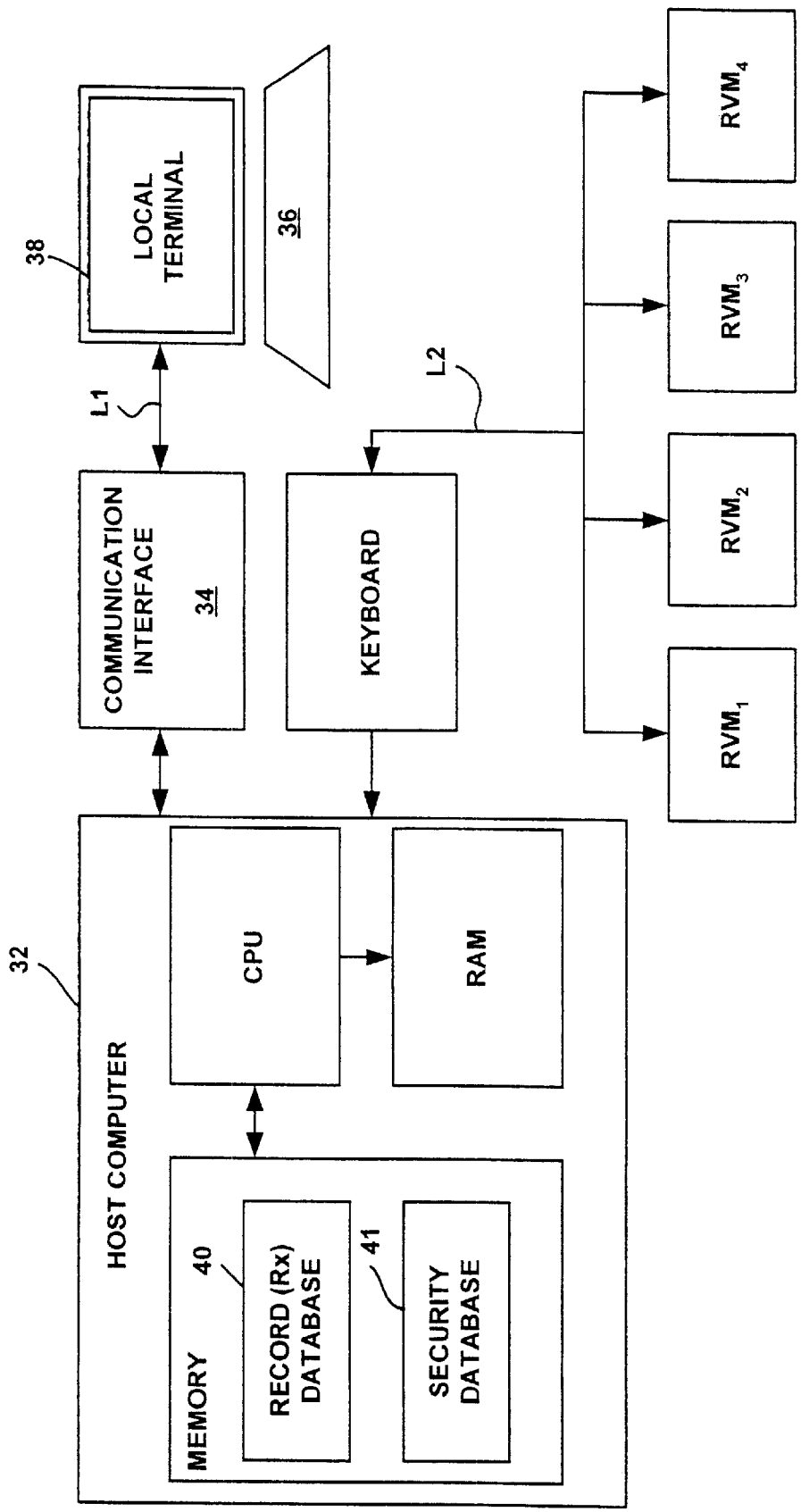
FIG. 3 is a schematic block diagram representing connectivity between RVM units at various sites and a centralized prescription filling facility in accordance an illustrative embodiment of the present invention.

With reference now to FIG. 3, there is shown an illustrative embodiment of the present invention which depicts the operation of a plurality of RVM units 10 under the direction of a centralized control facility. The primary components of the centralized control facility include a host computer 32 and a modem 34, with each RVM being also equipped with a modem and a label printer (FIG. 1). Using a data entry device, which may be a touch screen, keypad or, as in the illustrative embodiment, a keyboard 36, a user authorized via entry of an authenticated user ID and employing a local terminal 38 may enter a command to authorize the physical dispensing of an Rx that has been "digitally filled" by a registered pharmacist at a remote, centralized pharmacy, e.g. an online (Internet) pharmacy or mail order pharmacy. Illustratively, the user may be first required to enter an ID to be authenticated by the system prior to accepting any instructions or allowing any input.

In accordance with an especially preferred embodiment of the present invention, each patient is pre-assigned a static Patient Identification (PtID) key code which is used by that patient (or designated representative, e.g., a custodial parent) for all Rx transactions with that patient involving physical Rx drug preparation and consummation, by an RVM unit, of a "digitally filled" transaction. Each time a request is made for digital filling of an Rx for a given patient, local terminal 38 initiates creation of a new record which includes such conventional information as is normally required in the filling a prescription, including the patient's name, the drug, the dosage strength, instruction signature, and the prescribing physician's name. Each such record further includes a set of instructions which, when received by the RVM unit to which the patient goes for physical retrieval and consummation of a "digitally filled" prescription, enable the RVM unit to perform the requisite operating steps for the lawful fulfillment of the patient/consumer's physical Rx. In the illustrative embodiment of the present invention, each transaction record of a "digitally filled" Rx is stored in an encrypted format on centralized network database 40 to prevent unauthorized access and use. For each Rx "digitally filled" by a registered pharmacist via interaction with host computer 32 (for which Rx an encrypted record is stored in centralized database 40), a corresponding, specific and unique RxID key is stored in centralized database 40 to permit subsequent decryption and access by an RVM unit that has been activated by the consumer/patient in a manner which will now be described.

At the RVM unit selected by the consumer as the location for physical retrieval of a digitally filled Rx, the consumer is prompted to present proper identification in order to ensure that he or she is either a patient or an authorized representative of the patient. In the illustrative embodiment, such identification entails providing the PtID code, which may be performed, for example, by the consumer entering the code in its entirety via keypad 20 (FIG. 1) or by entering a shorter personal identification number (PIN) code in conjunction with insertion of an identification card readable by magnetic card reader 22. In any event, once the PtID code is provided, computer controller 30 is instructed by locally executed software to transmit this information over a suitable communications link, as internet communication link L11, to host computer 32 for authentication.

Authentication of the PtID code is performed, in a conventional manner, by executing a software program at host computer 32 that responds to receipt of the PtID by querying a network security database 41. In the event authentication is successful, an acknowledgement is transmitted to the RVM unit from which the authentication originated, and the. program instructs host computer 32 to query centralized database 40 to identify any "digitally filled" Rx transactions to be physically dispensed to the patient by the RVM unit. The program then instructs host computer 32 to transmit any encrypted records corresponding to the Rx transaction(s) so identified via communication link L1 to the patient/consumer activated RVM unit.

After receiving the encrypted record(s) via communication link L1, the RVM controller 30 of the activated RVM transmits an acknowledgment back to the host computer 32, along with a request that the host computer 32 transmit the corresponding RxID key code(s) that will allow the RVM to decode each Rx record and perform a sequence of dispensing. steps culminating in the physical dispensing of each "digitally filled" Rx. Upon receiving the RVM unit's request for an RxID key code, host computer 32 transmit the appropriate RxID key.

Using the RxID key, the RVM controller 30 decrypts the "locked" Rx data sent from the host computer 32 and, if appropriate, enables a dispensing actuator (not shown) to initiate the physical dispensing of an Rx in accordance, for example, with the operation described in U.S. Pat. No. 5,812,410 or 5,838,575. In accordance with such illustrative operation, the Rx vial containing drug product is capped, an Rx label printed and applied to the vial in an automated fashion, and finally, the Rx vial is ejected via a discharge opening where it is made available to the consumer/patient.

If desired, the host computer 32 may additionally instruct a printer local at the RVM unit to generate a document containing supplementary instructions for the patient. Modem 34 enables periodic or continuous communication between the host computer 32 and the RVM units of the network so that a complete inventory and status of each RVM unit is available at all times.

Figure 4:
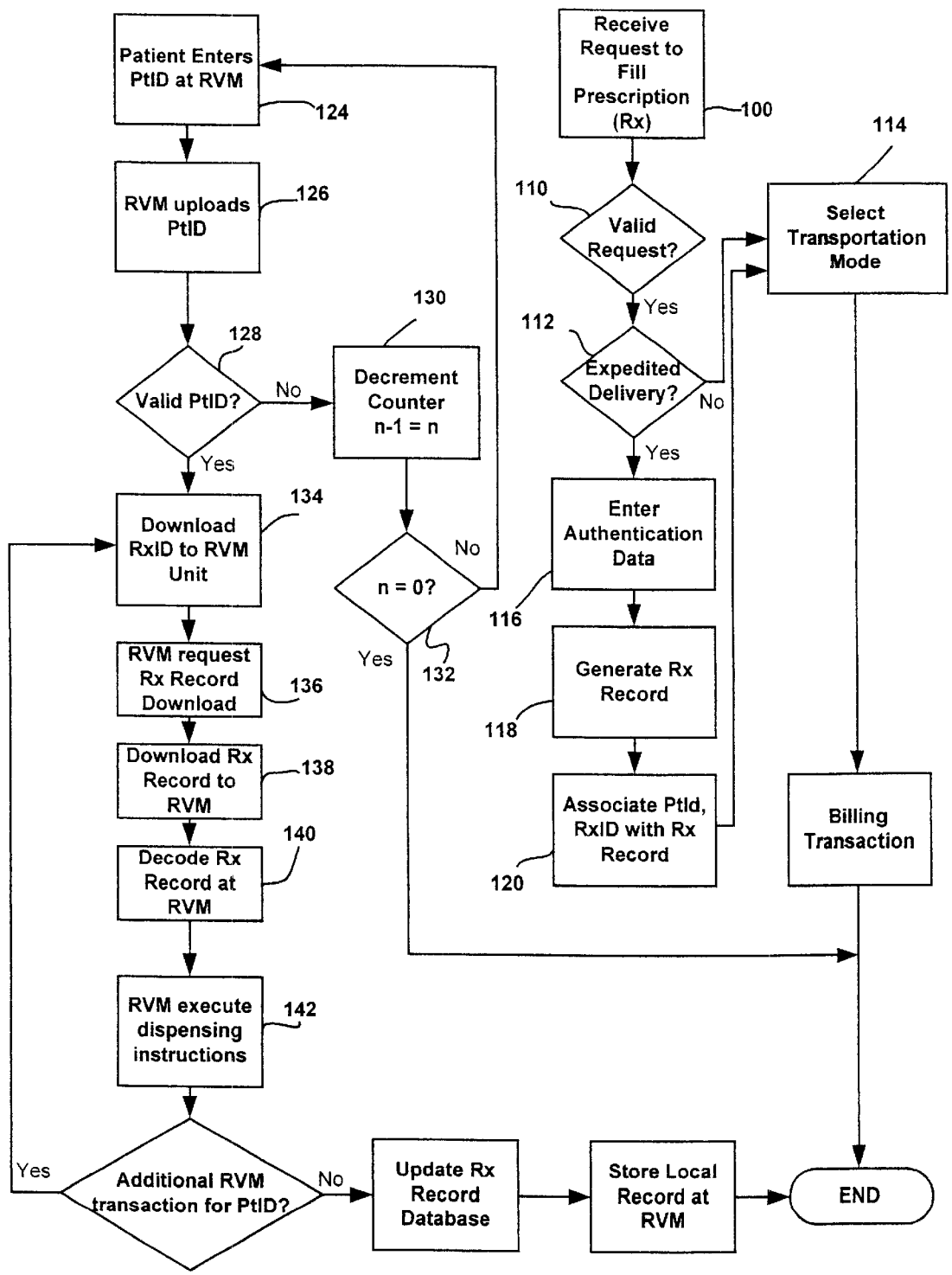
FIG. 4 is a flow chart depicting a sequence of operation of an integrated, prescription medication dispensing system employing the teachings of the present invention.

A flow chart depicting dispensing of medication in accordance with an illustrative embodiment of the present invention is depicted in FIG. 4. The process is entered at step 100, wherein a user licensed to fill prescriptions such, for example, as a pharmacist associated with an online Internet pharmacy or a mail-order pharmacy receives, either from a patient/consumer or directly from the prescribing physician, a request to fill a prescription. The request may be accompanied by a copy of the prescription form completed by the physician (as might be transmitted to a mail order or "cyber" pharmacist via facsimile, secure e-mail, or the like). In decision block 110, the pharmacist verifies the validity of the Rx request submitted as, for example, by contacting the prescribing physician. If the request is valid and the consumer is indeed appropriately requesting the prescribed medication, the process passes to decision block 112, whereupon during the "digital filling" of the Rx by the pharmacist the appropriate method of delivery of the Rx to the patient/consumer via regular mail, express courier, or customer pickup at an RVM unit, is selected. If the request is invalid at any step in the aforementioned authentication process, no action is taken on filling the Rx and the process terminates.

If the prescription request does not require immediate availability of the medication to the patient, then a conventional delivery method is selected (step 114) and the process terminates. If, however, immediate availability is required, then the mail order or cyber-pharmacist "digitally fills" the Rx by entering the appropriate information via keyboard 36. The Rx order waits in a secure computer database as a single or batch of digital Rxs to be later physically dispensed to a patient at any convenient RVM in the distributed network of remote RVM units. During an authentication step (block 116) the pharmacist inputs an ID code or provides some other entry (via an electronic card reader, bar code scanner, etc.) that establishes his or her authority to fill Rx requests, to fill Rx requests that have interoperability with the RVM units, as well as to operate the pharmacy host computer system. It should be noted that although a particular embodiment of the present invention in which there is no interaction between the patient user and the pharmacist at the time of physical filling the Rx that has been shown and described in detail, there is no requirement that such interaction be precluded. It may, in fact, be highly desirable to incorporate means for establishing real-time communication between the patient/consumer and the remote pharmacist to aid Rx dispensing and resolve various pharmaceutical care issues. For example, an audio-visual link using either a conventional telephone link or an Internet link may be employed. Additionally, an override capability may be included giving the remote pharmacist control over any aspect of the otherwise fully automated RVM operating process.

A record containing information relating to the identity of the patient and the identity of a given Rx to be dispensed, along with RVM directions in a format which, when properly decoded, provide the RVM units with the sequence of operating steps needed to physically dispense the required Rx, is then generated (block 118). As seen in block 120, a Prescription Identification (RxID) key uniquely assigned to the current Rx transaction and a Patient Indentification (PtID) permanently assigned to the patient/consumer are associated with the record generated in block 118. This information is transmitted, along with the record to centralized data base 40 (FIG. 3) (block 122).

In accordance with an especially preferred form of the invention, and as already mentioned above, the patient may fill his or her prescription at any of the RVM units associated with the network. Thus, after receiving the PtID key, the patient arrives at the RVM unit 10 of his or her choice and enters the PtID key code via the data entry panel thereof (block 124). This information is uploaded to host computer 32, whereupon it is cross-referenced to the "digitally filled" Rx data record database to determine if one or more digitally filled but physically unconsummated Rx transactions exist for that patient (block 126). In decision block 128, the results of the cross-referencing are either favorable or unfavorable. In the event of unfavorable authentication, the consumer is requested to re-enter the PtId code data again to re-initiate the authentication process (block 130). After three unsuccessful attempts (decision block 132), the RVM displays an appropriate denial of service message and the process is terminated. If the results of the cross referencing are favorable, the appropriate single or multiple RxID key(s) is/are transmitted to the RVM unit (block 130). If payment arrangements had not been previously made at the time of digitally filling the prescription, the patient may optionally be requested to insert a credit card into a magnetic card reader slot to complete a payment transaction.

After one or more RxID keys has been received, and payment arrangements confirmed or arranged, the RVM unit transmits a request for the host computer to download at least a first encrypted Rx data record. The first downloaded Rx data record is received by the RVM and unlocked locally with the corresponding RxID key, wherein at the RVM the Rx is physically consummated and dispensed to the patient. Once the patient has received the first Rx from an RVM, the RxID corresponding to that Rx physically dispensed to the patient, along with the corresponding PtID key, is noted in the database 40 as "DISPENSED & EXPIRED= RxID#########, RVM########, PtID#########, DATE:ddmmyy, and TIME:hh:mm:ss.

While the invention has been described with respect to a presently preferred construction and various considered modification and improvements thereto, still other constructions may also be suggested to those skilled in the art. For example, in an alternate configuration of the present invention, one or more of the RVM units may be manned by a simple cashier, with the Rx-filling transaction, including the appropriate authentication and verification steps, being remotely performed by a remote pharmacist. The invention should therefore not be narrowly construed to the foregoing description. Rather, the invention should be interpreted within the spirit and scope of the appended claims.

What is claimed is:

1. A method of dispensing medication to a patient, comprising the steps of:

receiving, at a first location, an Rx request to supply a patient with at least one package containing a drug prescribed by a physician;

creating a record comprising an encrypted file containing information relating to an Rx request received during the receiving step and instructions for enabling a remote drug dispensing machine to dispense the drug specified by a physician; and associating a unique Rx transaction key code with the record created during the creating step, said Rx transaction key code being adapted for use by a remote drug dispensing machine to decrypt said record.

2. The method of claim 1, further including transmitting the record and associated Rx transaction key code to a centralized processing facility and storing the record and associated Rx transaction key code in a centralized database at a centralized processing facility.

3. The method of claim 2, wherein said transmitting step is performed using an internet link.

4. The method of claim 2, further comprising:

transmitting, from a remote drug dispensing machine, a unique patient identification code corresponding to a patient for which a record and Rx transaction key code are stored at the centralized processing facility; and transmitting to the remote drug dispensing machine, in response to receiving the unique patient identification code at the centralized processing facility, an encrypted record containing instructions for operating the drug dispensing machine and a unique Rx transaction key corresponding thereto.

5. The method of claim 4, further comprising a step of decoding the record at the drug dispensing machine using the unique Rx transaction key code and performing a drug dispensing operation in accordance with instructions contained in the decoded record.

6. The method of claim 1, further including a step of creating and storing a receipt record locally at the remote drug dispensing machine, said receipt record containing an identity of a receiving patient, an identity of at least one drug dispensed, and a time and date the at least one drug was dispensed.

* * * * *